United States Patent [19]
Thompson et al.

[11] Patent Number: 5,735,884
[45] Date of Patent: Apr. 7, 1998

[54] FILTERED FEEDTHROUGH ASSEMBLY FOR IMPLANTABLE MEDICAL DEVICE

[75] Inventors: David L. Thompson, Fridley, Minn.; Robert T. Sawchuk, Phoenix, Ariz.; Lynn M. Seifried, Minneapolis, Minn.

[73] Assignee: Medtronic, Inc., Minneapolis, Minn.

[21] Appl. No.: 317,512

[22] Filed: Oct. 4, 1994

[51] Int. Cl.$^6$ .................................................. A61N 1/375
[52] U.S. Cl. ............................................................. 607/36
[58] Field of Search ................................. 607/1, 36, 37

[56] References Cited

U.S. PATENT DOCUMENTS

| | | | |
|---|---|---|---|
| Re. 32,378 | 3/1987 | Barthel | 128/419 |
| 3,538,464 | 11/1970 | Walsh | 333/79 |
| 3,546,638 | 12/1970 | Park | 333/79 |
| 3,945,387 | 3/1976 | Adams | 128/419 |
| 3,961,295 | 6/1976 | Hollyday et al. | 333/79 |
| 3,968,802 | 7/1976 | Ballis | 128/419 |
| 4,038,990 | 8/1977 | Thompson | 128/419 |
| 4,056,105 | 11/1977 | Ravas | 128/419 |
| 4,059,116 | 11/1977 | Adams | 128/419 |
| 4,079,343 | 3/1978 | Nijman | 333/79 |
| 4,144,509 | 3/1979 | Boutros | 333/181 |
| 4,187,481 | 2/1980 | Boutros | 333/182 |
| 4,222,626 | 9/1980 | Hollyday et al. | 339/147 |
| 4,320,763 | 3/1982 | Money | 128/419 |
| 4,328,807 | 5/1982 | Jirak et al. | 128/419 |
| 4,333,470 | 6/1982 | Barthel | 128/419 |
| 4,424,551 | 1/1984 | Stevenson et al. | 361/302 |
| 4,500,159 | 2/1985 | Briones et al. | 339/147 |
| 4,616,655 | 10/1986 | Weinberg et al. | 128/419 |
| 4,660,907 | 4/1987 | Belter | 339/14 |
| 4,678,868 | 7/1987 | Kraska et al. | 174/152 |
| 4,694,265 | 9/1987 | Kupper | 333/185 |
| 4,745,923 | 5/1988 | Winstrom | 128/419 |
| 4,750,495 | 6/1988 | Moore et al. | 128/419 |
| 4,796,630 | 1/1989 | Regna | 128/419 |
| 4,903,701 | 2/1990 | Moore et al. | 128/419 |
| 5,057,041 | 10/1991 | Yu et al. | 439/620 |
| 5,170,806 | 12/1992 | Colen | 128/901 |
| 5,184,285 | 2/1993 | Murphy et al. | 361/421 |
| 5,213,522 | 5/1993 | Kojima | 439/620 |
| 5,246,389 | 9/1993 | Briones | 439/620 |
| 5,336,253 | 8/1994 | Gordon et al. | 607/122 |

OTHER PUBLICATIONS

U.S. application, No. 8038373 date pending, Seifried et al.

*Primary Examiner*—William E. Kamm
*Attorney, Agent, or Firm*—Thomas F. Woods; Harold R. Patton

[57] ABSTRACT

A feedthrough configuration for a hermetically sealed implantable medical device which includes a metal case having an aperture and a feedthrough in the aperture which includes an electrically conductive pin, an insulating material supporting the pin, a block spaced from the case and in electrical continuity with the pin and a device for electrical protection connected to the block and to the case. The device for electrical protection preferably includes two zener diodes, a first diode connected at the block and a second diode connected to the case with an electrical conductor connecting the two diodes in a back-to-back configuration.

10 Claims, 4 Drawing Sheets

FILTERED FEEDTHROUGH ASSEMBLY FOR IMPLANTABLE MEDICAL DEVICE

BACKGROUND OF THE INVENTION

This invention relates generally to electrical medical devices and, more particularly, to feedthroughs for hermetically sealed electrical connections which provide electrical or EMI (electromagnetic interference) protection for such devices.

Implantable medical devices typically have a metal case and a connector block mounted to the metal case which includes receptacles for leads which may be used for electrical stimulation or sensing of physiological signals. Hermetically sealed within the case are the battery and the circuitry. To connect the leads outside the metal case with the circuitry and the battery inside the metal case, electrical feedthroughs are employed.

Electrical feedthroughs serve the purpose of providing an electrical circuit path extending from the interior of a hermetically sealed container to an external point outside the container while maintaining the hermetic seal of the container. The conductive path is provided through the feedthrough by a conductor pin which is electrically insulated from the container itself. Such feedthroughs typically include a ferrule which permits attachment of the feedthrough to the case, a conductor pin or lead and a hermetic glass or ceramic seal which supports the pin within the ferrule. One such feedthrough is that disclosed in U.S. Pat. No. 4,678,868 issued to Kraska et al in which a brazed alumina insulator provides hermetic sealing and electrical isolation of a niobium conductor pin from the case. Such feedthroughs are typically used in implantable pulse generators (IPG's) such as heart pacemakers or neurostimulators.

It has been discovered that such electrical devices can, under some circumstances, be susceptible to electromagnetic interference (EMI) such that its functioning is impaired. In particular, it has been found that EMI at specific frequencies can inhibit pacing in a heart pacemaker IPG and/or cause fast or erratic pacing. This problem can be addressed by incorporating a capacitor structure within the feedthrough ferrule thus shunting any EMI at the entrance to the IPG for high frequencies. A feedthrough/capacitor which can be used for such purposes is disclosed in U.S. Pat. No. 4,424,551 issued to Stephenson et al or in co-pending U.S. patent application Ser. No. 08/038,373, now U.S. Pat. No. 5,406,444, which places a toroidal capacitor directly into the feedthrough ferrule and around the pin with the capacitor electrically contacting the pin and the ferrule. However, such feedthrough/capacitors require many production steps and close tolerances and are therefore expensive and time consuming to manufacture.

In addition to the EMI which can cause malfunction of implantable medical devices, such medical devices also require protection against electrical interference from electrocautery and defibrillation pulses which can damage the circuitry of such devices. Such protection is typically provided by means of one or more zener diodes which are connected between the circuit to be protected and the case (or an indifferent electrode) in a manner which grounds voltage and current surges through the diode. The use of such diodes is disclosed in greater detail in U.S. Pat. Nos. 4,320,763; 4,328,807; 4,333,470; 4,745,923; 4,750,495; and 4,796,630. However, it would be desirable to provide a feedthrough which could be adapted to provide protection against this and other forms of electrical and electromagnetic interference.

It is therefore an object of the present invention to provide a feedthrough which effectively protects against interference from electrical sources.

It is also an object of the present invention to provide a feedthrough suitable for low cost production.

SUMMARY OF THE INVENTION

These and other objects have been accomplished by the protective feedthrough of the present invention. We have discovered a feedthrough configuration for a hermetically sealed implantable medical device which includes a metal case having an aperture and a feedthrough in the aperture which includes an electrically conductive pin extending through the aperture, an insulating material supporting the pin within the aperture, an electrically conductive block spaced from the case and in electrical continuity with the pin; and a device for electrical protection electrically connected at a first point to the block and electrically connected at a second point to the case. The device for electrical protection preferably comprises a first zener diode connected at a flat portion of the block, a second zener diode connected to the case, and an electrical conductor connected to each of the two diodes such the diodes are arranged in a back-to-back configuration.

A preferred embodiment of the invention also includes protection for electromagnetic interference. A device for electromagnetic protection such as a chip capacitor can be electrically connected at a first point to a peripheral upstanding portion of a ferrule mounted in the case aperture and electrically connected at a second point to a peripheral skirt portion of the block.

When multiple feedthroughs are to be provided with electrical protection, diodes can be applied to both feedthroughs and connected with a single case-mounted diode.

DETAILED DESCRIPTION OF THE INVENTION

Figure 1:
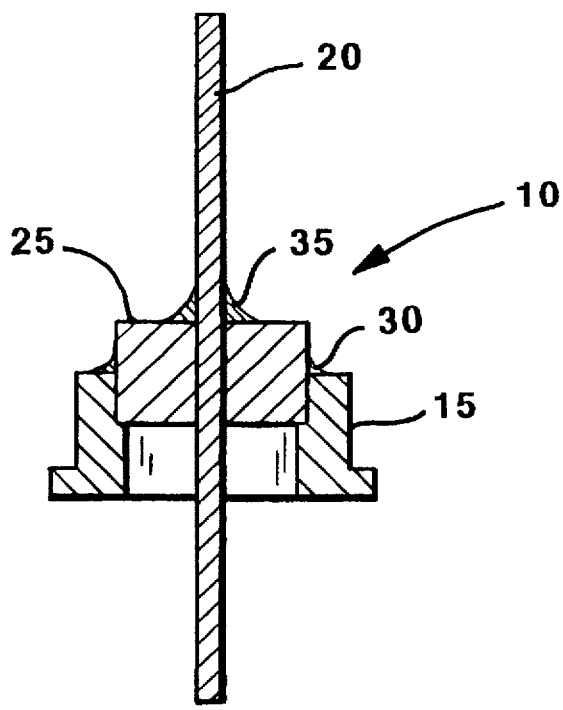
FIG. 1 is a cross-sectional view of a conventional feedthrough for an implantable medical device.
Figure 2:
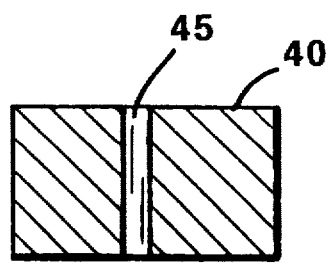
FIG. 2 is a cross-sectional view of an electrically conductive block used in the invention.
Figure 3:
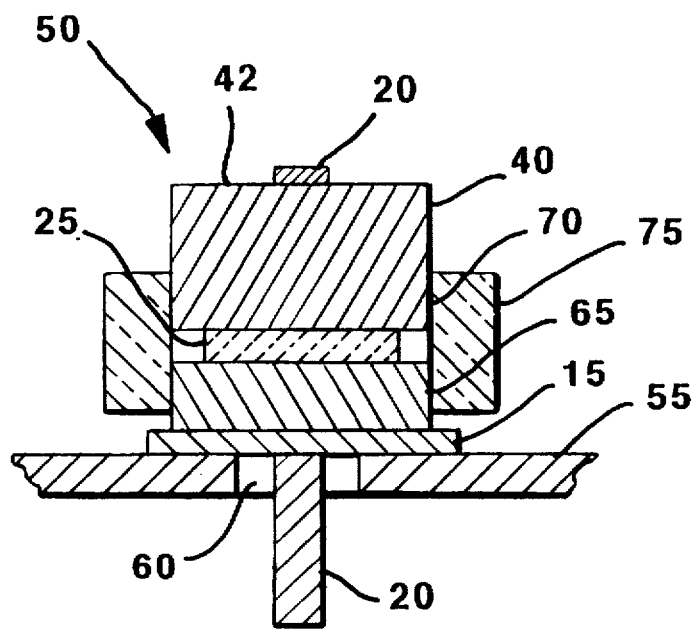
FIG. 3 is an elevational view of a feedthrough according to the invention.
Figure 4:
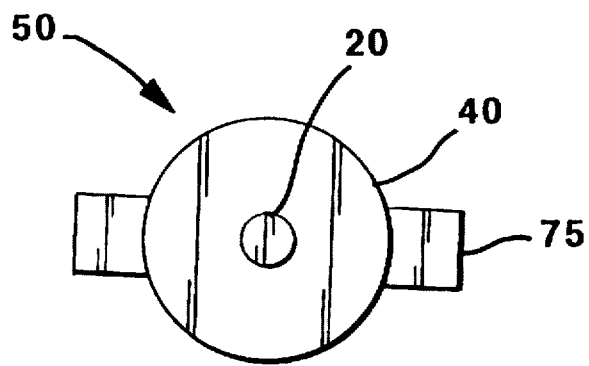
FIG. 4 is a top plan view of the feedthrough of FIG. 3.

The present invention relates to a feedthrough for a hermetically sealed implantable medical device. Such devices include a metal case of conventional design having an aperture containing a feedthrough. A durable metal case for an implantable medical device can be made of titanium or a titanium alloy. In the prior art, a suitable feedthrough for such a device is the brazed alumina feedthrough set forth in U.S. Pat. No. 4,678,868 issued to Kraska et al which is incorporated herein in its entirety. A similar feedthrough 10 is shown in FIG. 1 in which a ferrule 15 is disposed around a pin 20 which is supported by an insulator 25. The insulator 25 is secured to the ferrule 15 by means of a braze joint 30. Similarly, the pin 20 is secured to the insulator 25 by means of a braze joint 35. A feedthrough according to the present invention can be made from the feedthrough 10 of FIG. 1 by adding a block 40 as shown in FIG. 2 which has an aperture 45 adapted to accept the pin 20 of the feedthrough 10 of FIG. 1. The block 40 is made from an electrically conductive material that is solderable or weldable or may be wire-bonded to leads from the circuitry components of the device. For example, niobium or nickel would be satisfactory block materials. Preferably, the block 40 has a flat top portion 42 which allows electrical connections to be readily made to that portion of the block 40. The pin 20 can then be brazed, soldered or otherwise electrically attached to the block 40 and, if necessary, any excess length of the pin 20 can then be removed. FIGS. 3 and 4 show this feedthrough construction more clearly with the block 40 seated against the insulator 25 such that it is spaced from the ferrule 15 by the insulator 25. The resulting feedthrough 50 is in sealing engagement with one side of the case 55 while the pin 20 projects through an aperture 60 in the case 55. Typically, the ferrule 15 is sealed to the case by welding. In this arrangement, the ferrule 15 is shown to have a peripheral portion 65 which is upstanding from the surface of the case 55 while the block has a peripheral skirt portion 70 adjacent to the upstanding peripheral portion 65 of the ferrule and in linear alignment with the peripheral portion 65 of the ferrule. A device for electrical or electromagnetic protection 75 is electrically connected to the peripheral portion 65 of the ferrule 15 and also electrically connected to the peripheral skirt portion 70 of the block 40.

Figure 5:
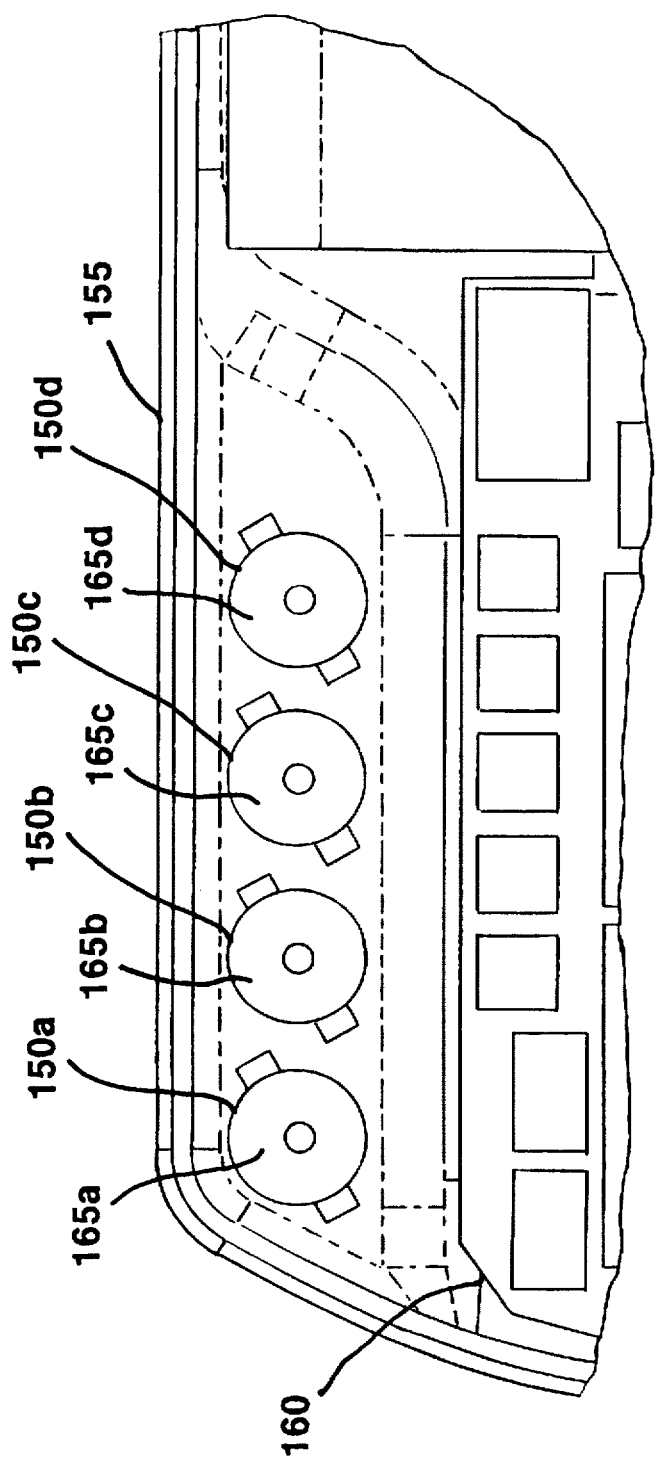
FIG. 5 is a partial plan view of a case assembly for an implantable medical device with included feedthrough array and circuitry.

FIG. 5 shows a linear array of feedthroughs 150a–d mounted in a case 155. A hybrid circuit assembly 160 is also mounted in the case 155 with their conductive block portions 165a–d spaced apart from the circuit assembly 160. Connections can be made from the circuit assembly 160 to the individual feedthroughs 150a–d by means of conventional electrical conductor materials affixed to the block portions 165a–d. Preferably, the block portions 165a–d have flat top portions to provide a surface for easy connections with electrical conductors.

One preferred device for electrical or electromagnetic protection in the present invention is a capacitor such as a chip capacitor which can be incorporated with the feedthrough as shown in FIGS. 3 and 4. Such chip capacitors can be attached at each end to the block and ferrule elements of the feedthrough by the use of a conductive epoxy adhesive. Other methods of attachment, such as soldering, are also acceptable. Preferably, more than one chip capacitor is used in order to provide improved EMI protection. Two, three or even four chip capacitors can be used as needed. When used in a linear array of feedthroughs as shown in FIG. 5, the array can be provided in a compact form by orienting the feedthroughs such that the chip capacitors are offset from the linear axis of the array. Feedthroughs provided with chip capacitors with combined capacitances in the range of about 1–4 nF were tested for insertion loss performance in various capacitor configurations with the average results set forth in Table 1.

TABLE 1

| Capacitor Configuration | Average Insertion Loss Performance (db) | | | |
| --- | --- | --- | --- | --- |
| | 3.5 MHz | 28.5 MHz | 450 MHz | 2540 MHz |
| 1-1nF | −2.0 | −12.5 | −26.4 | −20.0 |
| 2-1nF at 180° | −3.6 | −17.0 | −32.1 | −26.1 |
| 3-1nF at 90° | −5.9 | −20.7 | −35.6 | −33.7 |
| 4-1nF at 90° | −7.4 | −20.8 | −36.5 | −35.0 |
| 2-2nF at 180° | −8.6 | −20.6 | −24.6 | −30.8 |

Figure 6:
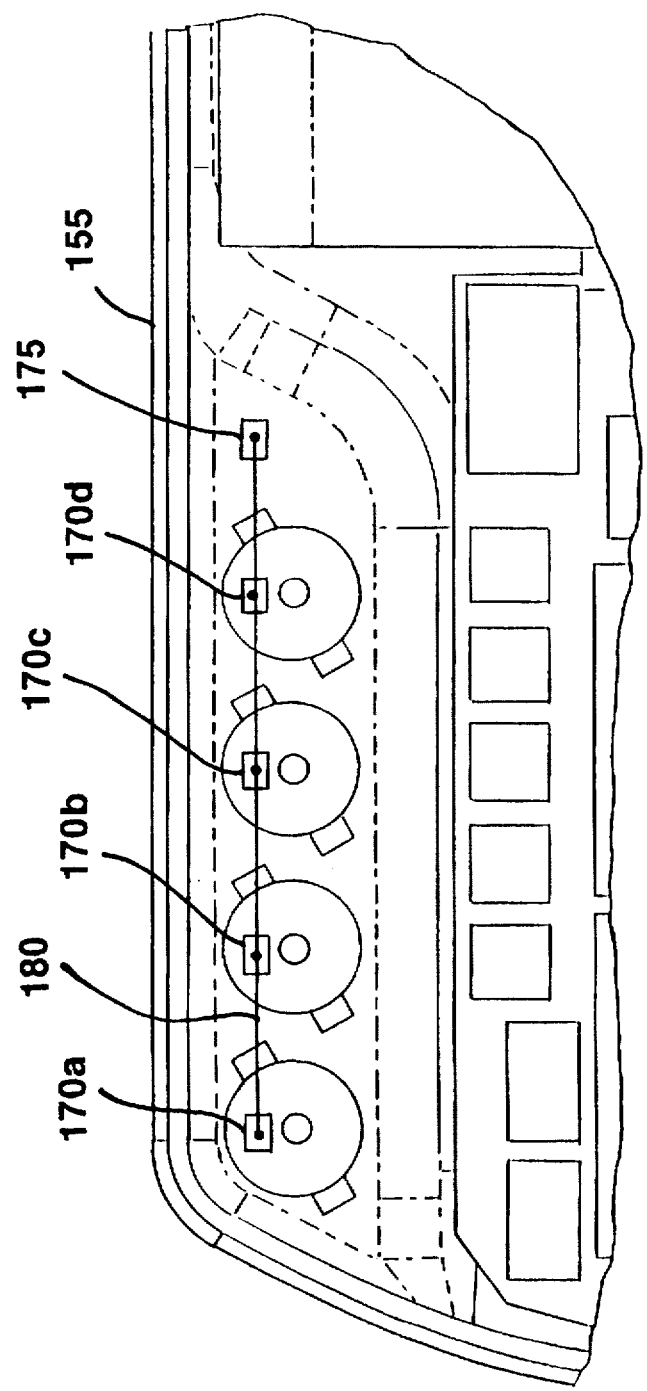
FIG. 6 is a partial plan view of a case assembly for an implantable medical device with included feedthrough array, zener diode array and circuitry.

In yet another application of protective devices to the feedthrough, protective devices can also be added to the block portion of the feedthrough as shown in FIG. 6. FIG. 6 shows single case zener diodes 170a–d (e.g. 0.38"×0.38" 10 V zener diodes) employed to provide protection against excessive voltage. The diodes 170a–d can be attached on one surface to the block portion of the feedthrough and on a second surface to a wire conductor 180 which joins the diodes 170a–d on the feedthrough array. These connections can be made by any suitable means for making electrical connections such as by soldering or conductive epoxy. The conductor 180 also extends to a similar diode 175 which has been electrically connected to the conductor 180 on one side and to the case 155 on a second side. The diodes thereby form the conventional back-to-back arrangement which break down at a predetermined voltage to provide protection against excessive voltage.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

We claim:

1. A feedthrough assembly disposed in an aperture of an hermetically sealed implantable medical device, the medical device comprising a metal case having an interior surface and an exterior surface, the aperture extending between the interior and exterior surfaces of the case, the feedthrough assembly comprising:

(1) an electrically conductive pin extending through the aperture such that the pin has a first end projecting from the exterior surface of the case and a second end projecting from the interior surface of the case;

(2) an insulating material supporting the pin within the aperture and in sealing engagement with the pin;

(3) an electrically conductive block spaced from the case and in electrical continuity with the pin; and (4) an electrical protection device electrically connected at a first point to the block and electrically connected at a second point to the case.

2. The feedthrough assembly according to claim 1 wherein the block has a flat portion to which the electrical protection device is connected.

3. The feedthrough assembly according to claim 1 wherein the electrical protection device comprises a first zener diode connected to the block, a second zener diode connected to the case, and an electrical conductor connected to each of the first and second diodes such the diodes are arranged in a back-to-back configuration.

4. The feedthrough assembly according to claim 3, wherein the feedthrough assembly is a first feedthrough assembly and a second feedthrough assembly having a third diode mounted thereon is positioned adjacent to the first feedthrough assembly, the diodes of the first and second feedthrough assemblies being electrically connected to the second diode.

5. The feedthrough assembly according to claim 1 wherein the electrical protection device is a chip capacitor.

6. A feedthrough assembly disposed in an aperture of an hermetically sealed implantable medical device, the medical device comprising a metal case having an interior surface and an exterior surface, the aperture extending between the interior and exterior surfaces of the case, the feedthrough assembly comprising:

(1) an electrically conductive pin extending through the aperture such that the pin has a first end projecting from the exterior surface of the case and a second end projecting from the interior surface of the case;

(2) an insulating material supporting the pin within the aperture and in sealing engagement with the pin;

(3) an electrically conductive block spaced from the case and in electrical continuity with the pin, the block having a peripheral skirt portion;

(4) an electrically conductive ferrule mounted in the aperture and in electrical continuity with the case, the ferrule having a peripheral upstanding portion; and (5) an electrical protection device electrically connected at a first point to the peripheral upstanding portion of the ferrule and electrically connected at a second point to the peripheral skirt portion of the block.

7. A feedthrough assembly disposed in a case aperture for an hermetically sealed implantable medical device, the device comprising a metal case having an interior surface and an exterior surface, the case aperture extending between the interior and exterior surfaces, the assembly comprising:

(1) an electrically conductive pin extending through the aperture such that the pin has a first end projecting from the exterior surface of the case and a second end projecting from the interior surface of the case;

(2) an insulating material supporting the pin within the aperture and in sealing engagement with the pin;

(3) a first zener diode mounted on the feedthrough assembly and in electrical continuity with the pin, a second zener diode mounted on and in electrical continuity with the case, and an electrical conductor connected to each of the first and second diodes such the diodes are arranged in a back-to-back configuration.

8. The feedthrough assembly according to claim 7 wherein the feedthrough assembly further comprises an electrically conductive block spaced from the case and in electrical continuity with the pin, the first diode being mounted on the block.

9. The feedthrough assembly according to claim 7 further comprising a chip capacitor electrically connected at a first point to the case and electrically connected at a second point to the pin.

10. The feedthrough assembly according to claim 7 wherein the feedthrough assembly is a first feedthrough assembly and a second feedthrough assembly having a third diode mounted thereon is positioned adjacent to the first feedthrough assembly, the diodes of the first and second feedthrough assemblies being electrically connected to the second case mounted diode.

* * * * *